US00PP33189P2

(12) United States Plant Patent
Smit

(10) Patent No.: US PP33,189 P2
(45) Date of Patent: Jun. 22, 2021

(54) ***BEGONIA* PLANT NAMED 'EC-BEGO-2009'**

(50) Latin Name: *Begonia masoniana*
Varietal Denomination: EC-BEGO-2009

(71) Applicant: Eden Collection, BV, Sappemeer (NL)

(72) Inventor: Obed Smit, Sappemeer (NL)

(73) Assignee: Eden Collection B.V.

( * ) Notice: Subject to any disclaimer, the term of this patent is extended or adjusted under 35 U.S.C. 154(b) by 0 days.

(21) Appl. No.: 17/036,571

(22) Filed: Sep. 29, 2020

(51) Int. Cl.
*A01H 5/12* (2018.01)
*A01H 6/18* (2018.01)

(52) U.S. Cl.
USPC ..... Plt./343
CPC ..... *A01H 6/185* (2018.05)

(58) Field of Classification Search
USPC ..... Plt./343
CPC ..... A01H 6/185
See application file for complete search history.

(56) References Cited

PUBLICATIONS

UPOV hit to a *Begonia* plant named, 'EC-BEGO-2009', QZ PBR 20200913, filed Mar. 30, 2020.*

* cited by examiner

*Primary Examiner* — Anne Marie Grunberg
(74) *Attorney, Agent, or Firm* — Cassandra Bright

(57) ABSTRACT

A new and distinct cultivar of *Begonia masoniana* plant named 'EC-BEGO-2009' is disclosed, characterized by an upper leaf surface color of brown tinged with dark yellow-green. Foliage is large with long, thick petioles and distinctly hairy and puckered on the supper surface. The new variety is a *Begonia*, and is normally used as an ornamental garden or container plant.

2 Drawing Sheets

Figure 1:
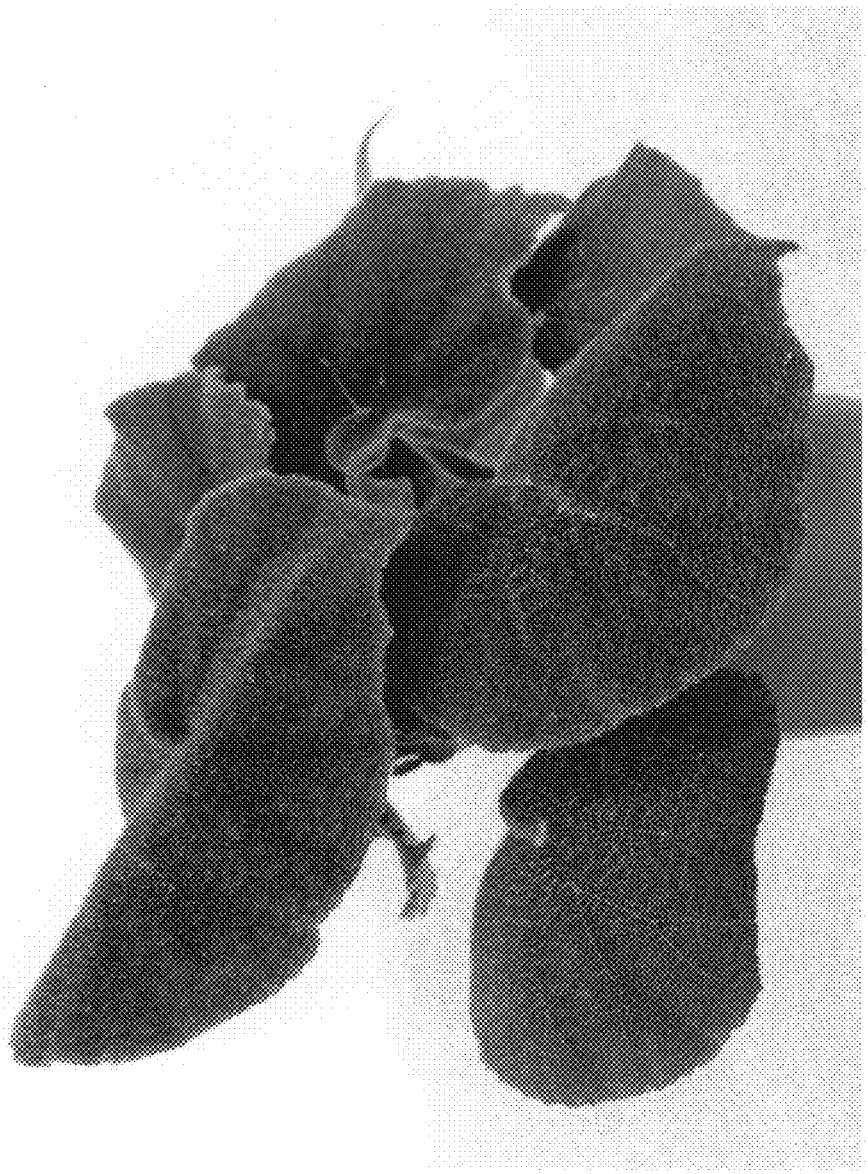

Latin name of the genus and species: *Begonia masoniana.*
Variety denomination: 'EC-BEGO-2009'.

BACKGROUND OF THE INVENTION

The new cultivar is the product of a planned breeding program. The new variety originated as the result of a crossing performed during 2014 of two proprietary, unpatented *Begonia masoniana* seedlings. The seed parent is the proprietary seedling referred to as "F". The pollen parent is the proprietary seedling referred to as "G". The selection of the new variety was made in 2017, by the inventor at a greenhouse located in Sappemeer, The Netherlands.

Asexual reproduction of the new cultivar 'EC-BEGO-2009' was first performed at a greenhouse in Sappemeer, The Netherlands by leaf cuttings during March 2017. 'EC-BEGO-2009' has since produced several generations and has shown that the unique features of this cultivar are stable and reproduced true to type.

SUMMARY OF THE INVENTION

The cultivar 'EC-BEGO-2009' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-BEGO-2009.' These characteristics in combination distinguish 'EC-BEGO-2009' as a new and distinct *Begonia masoniana* cultivar:

1. Solid upper leaf surface color, brown, tinged with dark yellow-green upper leaf surface.
2. Distinct hairy/puckered leaf upper surface.
3. Large foliage with long, thick petioles.

PARENT COMPARISON

Plants of the new cultivar 'EC-BEGO-2009' are similar to plants of the seed parent variety in most horticultural characteristics. However, plants of the new cultivar 'EC-BEGO-2009' differ in the following:

1. The new variety has a larger plant habit than the seed parent.
2. The new variety has a longer petiole than the seed parent.
3. The new variety has a lighter brown leaf color than the seed parent.
4. The new variety has larger foliage than the seed parent.

Plants of the new cultivar 'EC-BEGO-2009' are similar to plants of the pollen parent variety in most horticultural characteristics. However, plants of the new cultivar 'EC-BEGO-2009' differ in the following:

1. The new variety has brown foliage tinged yellow-green; the pollen parent has green foliage.
2. The new variety has slightly longer petioles than the pollen parent.
3. The new variety is a larger plant than the pollen parent.

COMMERCIAL COMPARISON

Plants of the new cultivar 'EC-BEGO-2009' are similar to plants of the unpatented commercial variety, *Begonia* 'Iron Cross', in most horticultural characteristics. However, plants of the new cultivar 'EC-BEGO-2009' differ in the following:

1. The new variety has a solid leaf color; this comparator has a cross-shaped central splotch.
2. The new variety is a significantly larger plant than this comparator.

Plants of the new cultivar 'EC-BEGO-2009' are similar to plants of the commercial variety, *Begonia maculata* 'EC-BEGO-1902', U.S. Plant Pat. No. 32,789 in most horticultural characteristics. However, plants of the new cultivar 'EC-BEGO-2009' differ in the following:

1. The new variety has solid colored leaves, while this comparator has a central splotch of radiating lines.
2. The new variety has solid colored foliage, this comparator has a different marginal coloration.

BRIEF DESCRIPTION OF THE PHOTOGRAPHS

The accompanying photograph in FIG. 1 illustrates in full color a typical plant of 'EC-BEGO-2009' grown in a greenhouse. The plant approximately 30 weeks of age.

Figure 2:
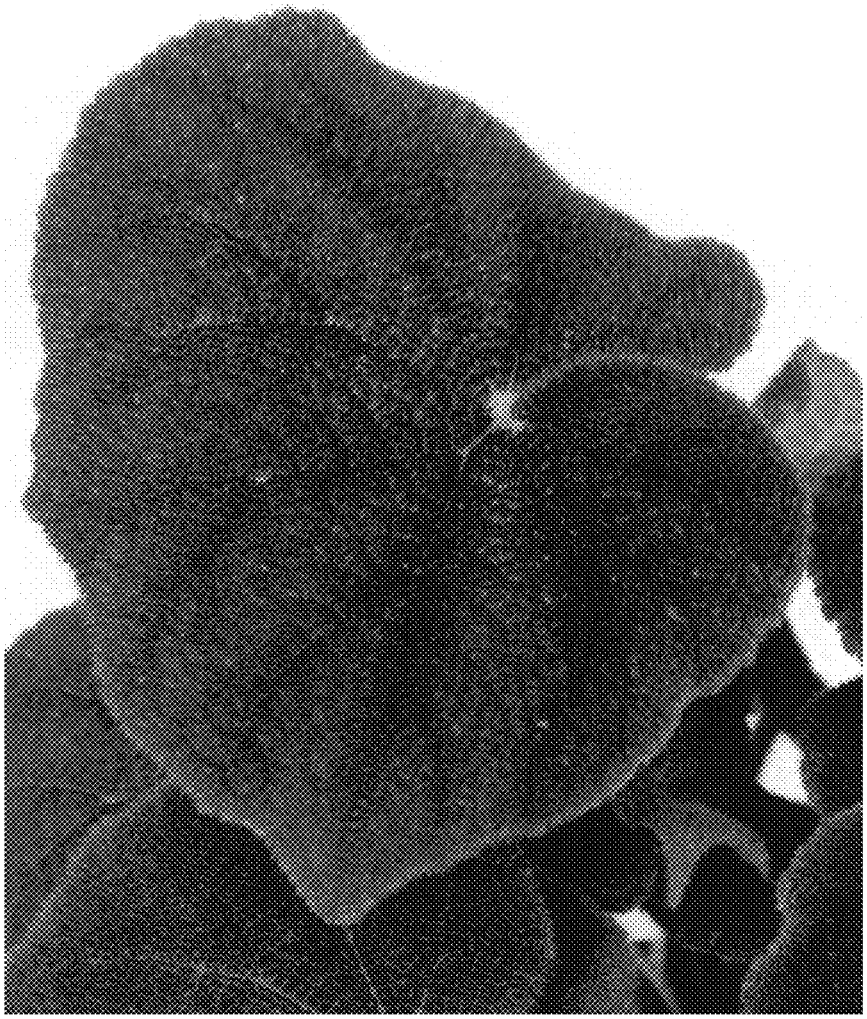

FIG. 2 illustrates a close up of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 30-week-old 'EC-BEGO-2009' plants grown in September in a greenhouse in Sappemeer, The Netherlands. Measurements and numerical values represent averages of typical plant types.

Botanical classification: *Begonia masoniana* 'EC-BEGO-2009'.

Age of plant described: Approximately 30 weeks.

Container size: 14 cm.

PROPAGATION

Type of propagation typically used: Leaf cuttings.

Time to develop roots: About 15 days at approximately 21° C. in Summer.

Time to develop a rooted liner: About 70 days at approximately 21° C. in Summer.

Root description: Herbaceous, fine, moderately dense, freely branching. Brown in color, not accurately measured with R.H.S. chart.

PLANT

Plant type: Perennial potted plant.

Growth habit: Flattened globular.

Height: 24.7 cm.

Plant spread: 35.3 cm.

Growth rate: Moderate.

Plant vigor: Moderate to high.

Branching characteristics: No branches; leaves grow directly from base.

FOLIAGE

Arrangement: Alternate, single, basally emerging.

Average length: Approximately 20 cm.

Average width: Approximately 15.5 cm.

Shape of blade: Broad ovate to near reniform.

Apex: Long apiculate.

Base: Oblique, lobes slightly to moderately overlapping.

Margin: Irregular shallow crenate, finely undulate, densely covered with short strigose hairs, average length 1.0 mm, colored RHS Greyed-Purple 187D.

Texture of top surface: Strongly papillose, on top of each papilla a single strigose hair is placed, average length: 1.0 mm, colored greyed-purple; 187D.

Texture of bottom surface: Densely covered with short hispid hairs, average length 1.0 mm, colored greyed-orange; N170D and lighter.

Rugosity:

*Upper side*.—Somewhat rugose.

*Under side*.—Somewhat rugose.

Luster:

*Upper side*.—Moderately shiny.

*Under side*.—Matte.

Color:

*Young foliage upper side*.—RHS Yellow-Green 152A, papillae greyed-orange 176A.

*Young foliage under side*.—RHS Greyed-Red 182A, fading to Orange-Red N34A at margins. Main veins Yellow-Green 145A and 149A.

*Mature foliage upper side*.—RHS Greyed-Brown N199B, strongly tinged Yellow-Green 147A.

*Mature foliage under side*.—RHS Greyed-Red 181C.

Venation:

*Type*.—Laciniate-reticulate.

*Venation color upper side*.—RHS Yellow-Green 147A.

*Venation color under side*.—RHS Yellow-Green 146C and 146D.

Petiole:

*Length*.—Approximately 16.5 cm.

*Diameter*.—Approximately 9 mm.

*Color*.—Upper side: RHS Mixture of Yellow-Green 148A and Grey-Brown 199A. Under side: RHS Mixture of Yellow-Green 148A and Grey-Brown 199A. Texture: Densely pubescent with strigose hairs, average length 3.0 mm, colored RHS Greyed-Green 195D. Luster: Slightly glossy. Strength: Low.

FLOWER

Not observed to date.

REPRODUCTIVE ORGANS

Not observed to date.

OTHER CHARACTERISTICS

Seeds and fruits: Not observed to date.

Disease/pest resistance: Neither resistance nor susceptibility to diseases or pests of *Begonia* has been observed in this variety.

Temperature tolerance: The new variety tolerates temperatures from approximately 5° to 35° C.

What is claimed is:

1. A new and distinct cultivar of *Begonia* plant named 'EC-BEGO-2009' as herein illustrated and described.

* * * * *